United States Patent [19]

Brain et al.

[11] 4,290,948
[45] Sep. 22, 1981

[54] PROCESS FOR THEIR PREPARATION OF β-LACTAM ANTIBACTERIAL AGENTS

[75] Inventors: Edward G. Brain, Reigate; Neal F. Osborne, Cranleigh, both of England

[73] Assignee: Beecham Group Limited, England

[21] Appl. No.: 91,978

[22] Filed: Nov. 7, 1979

[30] Foreign Application Priority Data

Nov. 22, 1978 [GB] United Kingdom ............... 45629/78

[51] Int. Cl.³ ........................................... C07D 499/00
[52] U.S. Cl. .............................. 260/245.2 R; 424/270; 424/271; 260/239 A
[58] Field of Search ................... 260/245.2 R; 424/270

[56] References Cited

U.S. PATENT DOCUMENTS 4,155,912  5/1979  Menarp et al. ...................... 424/270

FOREIGN PATENT DOCUMENTS 866845 11/1978 Belgium .
2210  6/1979 European Pat. Off. .
636  7/1979 European Pat. Off. .

Primary Examiner—Nicholas S. Rizzo
Attorney, Agent, or Firm—Jacobs & Jacobs

[57] ABSTRACT

A process for the preparation of the compounds of the formula (II):

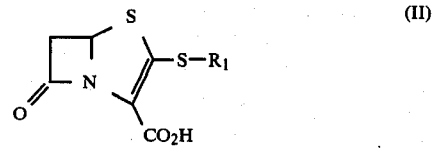

and salts and cleavable esters thereof wherein $R_1$ is a hydrocarbon group of up to 12 carbon atoms and which optionally also contain up to 4 heteroatoms selected from oxygen, nitrogen, sulphur or chlorine and bromine which process comprises the reaction of a cleavable ester of a compound of the formula (III):

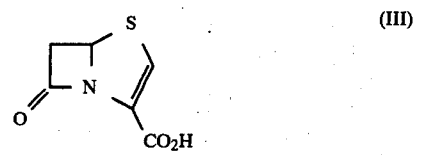

with one equivalent of a strong base of low nucleophilicity and thereafter with a compound of the formula (IV) or (V):

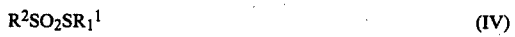

<br>
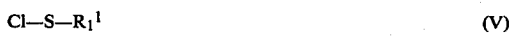

wherein $R_1^1$ is a group $R_1$ in which any amino substituent is protected and $R^2$ is an alkyl group of 1–4 carbon atoms optionally substituted by a phenyl group or is a phenyl group optionally substituted by an alkyl group of 1–4 carbon atoms and thereafter if desired cleaving the ester moiety to yield the acid of the formula (II) or a salt thereof and removing the protecting group from any protected amino group present in $R_1^1$; is described.

8 Claims, No Drawings

PROCESS FOR THEIR PREPARATION OF β-LACTAM ANTIBACTERIAL AGENTS

R. B. Woodward (Acta Pharm. Suecica, 1977, 14 Suppl., p 23-25) disclosed that the compounds of the formula (I):

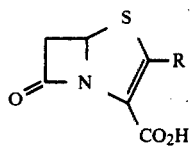

where R was an unspecified group possessed antibacterial activity. No aid in determining the nature of the group R was given by Professor Woodward nor did he describe the preparation of any compounds of the formula (I). However at the symposium on Current Topics in Drug Research (Uppsala, Sweden, Oct. 1977) Professor Woodward described the compound of the formula (I) wherein R is a hydrogen atom. We have prepared this compound and found it to possess a somewhat disappointing degree of antibacterial activity. European Patent Application No. 0000636 disclosed certain compounds of the formula (I) wherein R is an alkyl group and U.S. Pat. No. 4155912 demonstrates that a compound of the formula (I) wherein R is a methyl group is orally absorbed. Compounds of the formula (I) wherein R is an alkylthio group were mentioned briefly in European Patent Application No. 0002210 and Belgian Pat. No. 866845. The processes disclosed for the preparation of compounds of the formula (I) wherein R is a substituted thio group comprised the cyclisation of monocyclic esters. We have found an alternative and versatile process that allows the preparation of compounds of the formula (I) wherein R is a substituted thio group.

Accordingly the present invention provides a process for the preparation of the compounds of the formula (II):

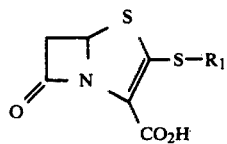

and salts and cleavable esters thereof wherein $R_1$ is a hydrocarbon group of up to 12 carbon atoms and which optionally also contain up to 4 heteroatoms selected from oxygen, nitrogen, sulphur or chlorine and bromine which process comprises the reaction of a cleavable ester of a compound of the formula (III):

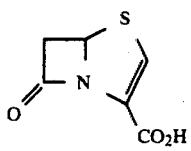

with one equivalent of a strong base of low nucleophilicity and thereafter with a compound of the formula (IV) or (V):

$$R^2SO_2SR_1{}^1 \qquad \text{(IV)}$$

$$Cl-S-R_1{}^1 \qquad \text{(V)}$$

wherein $R_1{}^1$ is a group $R_1$ in which any amino substituent is protected and $R^2$ is an alkyl group of 1-4 carbon atoms optionally substituted by a phenyl group or is a phenyl group optionally substituted by an alkyl group of 1-4 carbon atoms and thereafter if desired cleaving the ester moiety to yield the acid of the formula (II) or a salt thereof and removing the protecting group from any protected amino group present in $R_1{}^1$.

Apt groups of the formula $R_1$ include alkyl groups of up to 4 carbon atoms; alkenyl groups of up to 4 carbon atoms; alkyl groups of up to 4 carbon atoms substituted other than on the α-carbon atom by an amino or acetylamino group; alkyl group of up to 4 carbon atoms substituted by an alkoxycarbonyl group wherein the alkoxy part contains up to 4 carbon atoms; alkenyl groups of up to 4 carbon atoms substituted other than on the α-carbon atom by an acetylamino group; alkenyl groups of up to 4 carbon atoms substituted by an alkoxycarbonyl group wherein the alkoxyl part contains up to 4 carbon atoms; a phenyl group; a phenyl group substituted by a methyl, amino, alkoxycarbonyl wherein the alkoxy part contains up to 4 carbon atoms, acetamino or methoxyl groups or by a chlorine or bromine atom; a pyridyl group; or a pyrimidyl group.

$R_1$ groups worthy of mention include the methyl, ethyl, n-propyl, β-aminoethyl, β-acetamidoethyl, and phenyl groups.

Suitable cleavable ester groups include those removable by hydrogenolysis, those removable by hydrolysis and those removable by fluoride ion. Esters conventionally removable by hydrogenolysis include benzyl esters. Esters removable by hydrolysis include trimethylsilyl esters. The tert-butyldiphenylsilyl ester is particularly apt as it is readily cleavable by treatment with fluoride ion.

Antibacterially active esters of the compounds of the formula (II) are believed to be those cleavable by in-vivo hydrolysis to the compounds of the formula (II) or their salt. Such esters may be identified by administration to a test animal such as a rat or a mouse by intravenous administration and thereafter examining the test animals body fluids for the presence of the compound of the formula (II) or its salt.

Suitable esters of this type include those of the part formulae (a) and (b):

$$-CO-O-CHA_1-O-CO-A_2 \qquad \text{(a)}$$

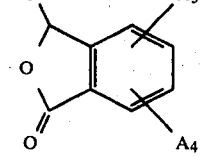

where $A_1$ is a hydrogen atom or a methyl group, $A_2$ is an alkyl or alkoxy group of 1-4 carbon atoms or a phenyl group, $A_3$ is a hydrogen atom or a methyl or methoxyl group and $A_4$ is a hydrogen atom or a methyl or methoxyl group. Other esters of the compounds of the formula (II) of interest are those cleavable by chemical methods as described hereinafter.

Aptly R² in the compound of formula (IV) is a methyl or p-tolyl group and preferably is a methyl group.

The base used in the reaction may be n-butyl lithium or a chemically equivalent agent.

The reaction is normally carried out in an aprotic medium at a depressed temperature, for example −70°–100° C., for example in dry tetrahydrofuran at −95°. Under these conditions the ester of the compound of the formula (III) need be in contact with the base for not more than 2 minutes before the compound of the formula (IV) or (V) is added After a further short time, for example less than 1 minute, the reaction mixture may be quenched with a little acetic acid. The reaction mixture may then be diluted with a water immiscible organic solvent such as ethyl acetate and the mixture then washed with water to remove water soluble impurities. The product may then be obtained by evaporation of the solvent. Purification of the product may then be carried out chromatographically, for example on silica gel eluting with ethyl acetate/petroleum ether.

The thus produced ester may then be cleaved to yield the corresponding acid or its salts. We prefer to use the tertbutyldiphenylsilyl ester which is cleavable by treatment with anhydrous potassium fluoride in dry tetrahydrofuran at ambient temperature in the presence of a crown ether. The desired salt can then be obtained by evaporation of the solvent followed by trituration under dry ether. Further purification can be effected chromatographically if desired.

The potassium salt produced in this manner above may be converted into other salts in conventional manner, for example by ion-exchange using an ion-exchange resin such as IR-120 in the form of its sodium, calcium, magnesium, or like salt. Similarly the potassium salt may be converted into the acid by careful acidification of an aqueous solution and concomitant extraction of the acid into ethyl acetate from which it may be recovered by evaporation after drying.

From the foregoing it will be realised that certain favoured intermediates of this invention are the silyl esters of the compound of the formula (II). Of these esters the tertbutyldiphenylsilyl ester is particularly suitable.

In an alternative aspect the present invention provides the preparation of silyl esters of the compound of the formula (III) which process comprises reacting a salt of the compound of the formula (III) with a silylating reagent.

Apt silylating reagents include silyl halides, for example chlorides such as tert-butyldiphenylsilyl chloride. Suitably the silylation is carried out in an aprotic medium such as methylene chloride at an ambient temperature. The desired silyl ester may be obtained by evaporation of the solvent. The use of the tertbutyldiphenylsilyl ester or like water stable ester allows for purification by dissolving in ethyl acetate, filtering, and then washing with water. The dried organic layer may then be evaporated and further purified by chromatography on silica gel eluting with ethyl acetate/petroleum ether.

The salt of the compound of the formula (II) may be prepared as outlined in Scheme 1 hereinafter.

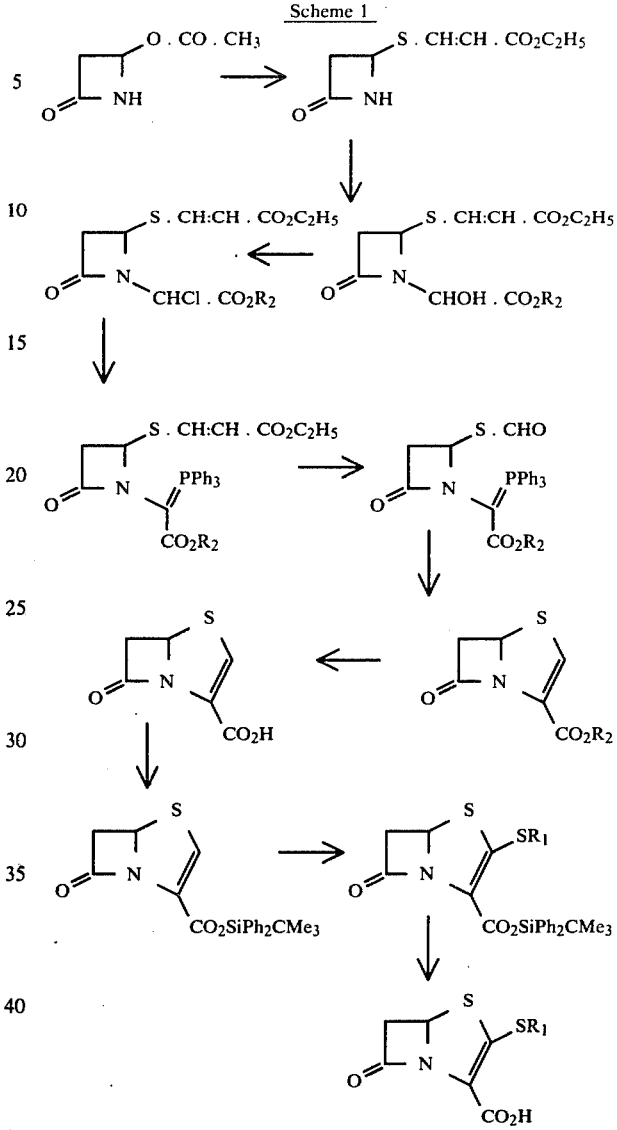

Scheme 1

It is believed that the more active isomer of the compound of the formula (II) is that of the formula (VI):

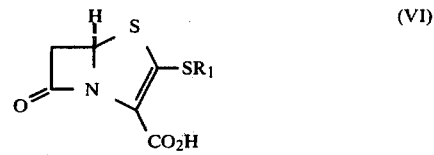

(VI)

and salts and cleavable esters thereof wherein $R_1$ is as defined in relation to formula (II). The desired isomer may be obtained by using the appropriate optical form of the compound of the formula (III) (see for example Belgian Patent No. 866845) or by resolution of the compound of the formula (II) or its salt or cleavable ester.

The compounds produced by the process of this invention may be used in a pharmaceutical composition which comprises a compound of the formula (II) or a pharmaceutically acceptable salt or in-vivo hydrolysable ester thereof and a pharmaceutically acceptable carrier.

Most suitably the composition of this invention comprises a compound of the formula (II) or a pharmaceutically acceptable salt thereof. It is particularly suitable that the compositions of this invention comprises a sodium or potassium salt of a compound of the formula (II).

The compositions of this invention may be in a form suitable for injection or for oral administration such as tablets or capsules. In general such compositions are in unit dose form and contain from 50 mg to 1000 mg and more usually from 100 mg to 500 mg. Such compositions may be administered once or more times per day so that the daily dose for a 70 kg adult is in the range 500 mg to 2500 mg.

The compositions of this invention may be formulated in the manner of known antibiotics such as ampicillin. Thus for example an injectable solution may be prepared by dissolving 100 mgs of a sodium salt of a compound of the formula (II), for example that where $R^1$ is a methyl group, in sterile water for injection BP. Alternatively, such a compound may be formulated into a tablet or capsule in standard manner with such excipients as lubricant, disintegrant, filler, binder or the like, for example magnesium stearate, microcrystalline cellulose, sodium starch glycollate, polyvinylpyrrolidone, polyvinylpolypyrrolidone or the like.

In the following illustrative examples all column chromatography was carried out using Merck Silica gel 60 (7729). Petroleum ether means petroleum ether b.p. 60°–80°. PNB means p-nitrobenzyl.

Examples 1–8 illustrate a known process for the purpose of comparison. Examples 9–18 and 22 illustrate the preparation of useful intermediates. Examples 19–21 and 23–26 illustrate the process of this invention.

EXAMPLE 1

4-Ethyltrithiocarbonatoazetidine-2-one

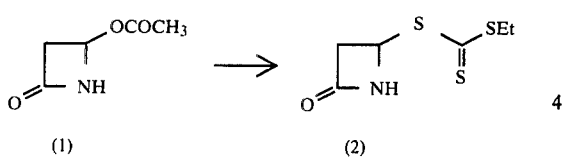

To a solution of potassium hydroxide (0.45 g. 1 eq) and ethane thiol (0.6 ml 1 eq) in ethanol (15 ml) was added carbon disulphide (0.5 ml, 1.03 eq). After ½ hour the bright yellow solution was diluted to 20 ml with ethanol and added at 0° to a stirred solution of 4-acetoxyazetidin-2-one (1) (1.0 g, 1 eq) in ethanol (10 ml). After 1 hour at 0° and ½ hour at room temperature the mixture was evaporated to a gum in vacuo. The residue was partitioned between ethyl acetate and water then the solvent layer was dried (Mg 504) and evaporated to give the desired trithiocarbonate (2) as yellow needles m.p. 107° (ex ethyl acetate-petroleum ether) (0.82 g, 51%) (Found C, 35.06; H, 4.47; N, 6.77, S, 43.30. $C_6H_9NOS_3$ requires C, 34.78; H, 4.35; N, 6.76; S, 46.38%) $\lambda_{max}$ (EtOH) 240 nm (Em3, 280), 302 nm (13,100) $\nu$ max (CHCl$_3$) 3410, 1780 (b) $\delta$ ppm (CDCl$_3$) 1.35 (3H, t J 7 Hz) 2.98 L (ddd, J 9, 3, 1 Hz) 3.36 (qu. J 7 Hz) 3.50 (ddd J 9, 5, 2, Hz) together 4H., 5.55 (1H, dd J 5,3, Hz) 6.75 (b.m. 1H exch D$_2$O).

EXAMPLE 2

1-(1-t-Butoxycarbonyl-1-hydroxy-methyl)-4-ethyltrithiocarbonatoazetidine-2-one

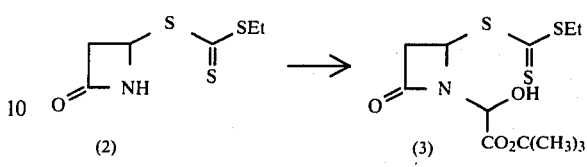

A mixture of the trithiocarbonateazetidinone (2) (100 mg) and t-butyl glyoxylate (600 mg) in benzene (20 ml) was refluxed for 24 hours using a Dean & Stark water separator. The reaction mixture was washed with 6 × 10 ml water, dried and evaporated: then the residue was chromatographed eluting with 20% ethyl acetate/petroleum ether.

In this way the pure hydroxy-ester (3) was obtained as an oil (153 mg 93%) $\nu$ max (CHll$_3$) 3500 (b) 1775, 1735 cm$^{-1}$. n.m.r. shows a mixture of sterioisomers in approx. 3:4 ratio $\delta$ ppm (CDCl$_3$) 1.36 (t, J=7 Hz) 1.5 (S) together 12H, 3.17 (dd, J=16,2 Hz) 3.4 (qu J=7 Hz) 3.68 (dd J=16, 5 Hz) together 4H, 4.2 (1H b.s. exch. D$_2$O) 5.23 and 5.4 (2S, 1 H) 5.98 and 6.14 (1H, 2dd, J=5, 2 Hz).

EXAMPLE 3

1-(1-t-Butoxycarbonyl-1-triphenylphosphoramylidenemethyl)-4-ethyltrithiocarbonatoazetidine-2-one

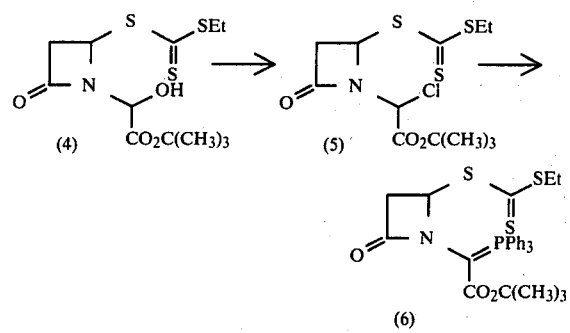

The hydroxy-ester (4) (220 mg) in tetrahydrofuran (10 ml) at −20° under argon was treated first with lutidine (140 mg, 2 equivalents) followed by thionyl chloride (0.096 ml, 2 equivalents) diluted with a little tetrahydrofuran.

After 30 minutes, conversion to the chloride (5) was complete (by t.l.c.). The mixture was therefore filtered and evaporated to dryness in vacuo at room temperature to give the chloride (5) as an oily residue $\nu$ max (CHCl$_3$) 1780, 1745 cm$^{-1}$.

The total crude product was treated with lutidine (105 mg, 1.5 equivalents) and triphenylphosphine (260 mg. 1.5 equivalents) in dioxan (20 ml) at 50° under argon for 24 hours. The reaction mixture was filtered and evaporated to dryness in vacuo then the residue was chromatographed on silica gel eluting with 20–60% ethyl acetate/petroleum ether. The desired phosphorane (6) (191 mg) was obtained as an amorphous bright yellow solid. $\nu$ max (CHCl$_3$) 1750, 1635, 1610 cm$^{-1}$.

EXAMPLE 4 t-Butyl 2-ethylthiopenem-3-carboxylate

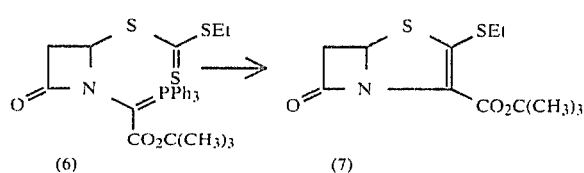

The phosphorane (6) (230 mg) was heated in xylene under argon using an oil bath maintained at 140°. After 6 hours the solution was concentrated in vacuo and the gummy residue chromatographed on silica gel, eluting with 40–50% ethyl acetate/petroleum ether. In this way the desired penem ester (7) was isolated as a gum (19 mg. 20%) Found M+287.0665 $C_{12}H_{17}NO_3S_2$ requires 287.0650 λmax (EtOH) 257 (E=6370), 335 (7780) νmax (CHCl₃) 1790, 1680 cm⁻¹ δppm 1.36(t) 1.52 (S) 2.92 (qu J=7Hz) 3.39 (dd J=17. 2 Hz) 3.75 (dd, J=17, 4 Hz) 5.64 (dd J=4,2 Hz).

From the faster-running fractions was also obtained triphenylphosphine sulphide 50 mg (59%) m.p. 162°

EXAMPLE 5

1-(1p-Nitrobenzyloxycarbonyl-1-hydroxy-methyl)-4-ethyltrithiocarbonatoazetidine-2-one

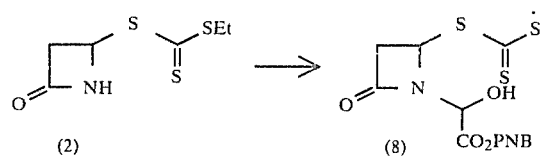

A mixture of the thithiocarbonatoazetidinone (2) (1.25 g) and p-nitrobenzyl glyoxylate (2.5 g) in benzene (100 ml) was refluxed for 24 hours using a Dean & Stark water separator. The product was separated as in Example 2. The hydroxy-ester (8) was obtained as a semi-solid Mixture of diastereoisomers (1.6 g, 64%) νmax (CHCl₃) 3520, 1780, 1760 cm⁻¹. δppm (CDCl₃) 1.36 (3H, t J=7 Hz), 3.10 (dd, J=16, 2 Hz), 3.36 (qu. J=7 Hz), 3.67 (dd, J=16, 5), together 4H, 4.8 (1H, b.m. sharpens to 2S with D₂O) 4.2 (1H, b.m. exch D₂O) 5.31 and 5.40 (2H, 2S) 5.98 and 6.07 (1H, 2dd, J=5, 2 Hz) 7.9–8.4 (4Hm).

EXAMPLE 6

1-(1-p-Nitrobenzyloxycarbonyl-1-triphenylphosphoranylidenemethyl)-4-ethyltrithiocarbonatoazetidine-2-one

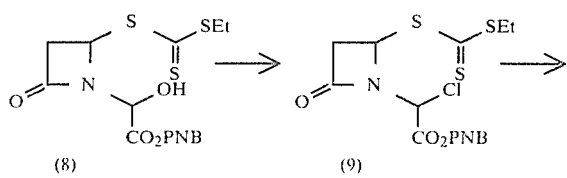

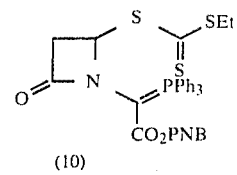

The hydroxy-ester (8) (1.6 g) in tetrahydrofuran (30 ml) at −20° under argon was treated successively with lutidine (0.62 g, 1.5 equivalents) followed by thionyl chloride (0.42 ml 1.5 equivalents), in the same way as Example 3. The crude chloride μmax (CHCl₃) 1790, 1779 cm⁻¹ was treated with triphenylphosphine (1.52 g 1.5 equivalents) and lutidine (0.62 g 1.5 equivalents) at 60° in dioxan under argon for 24 hour. The desired phosphorane (10) was obtained as in Example 3 (1.15 g, 45%) fine yellow crystals m.p. 227°–229° ex ethyl acetate νmax (CHCl₃) 1760 (b) 1620 (b) cm⁻¹. (Found: C, 60.0; H, 4.6; N, 4.2% $C_{33}H_{29}N_2O_5S_3P$ requires: C, 60.0; H, 4.4; N, 4.2%).

EXAMPLE 7 p-Nitrobenzyl 2-ethylthiopenem-3-carbonylate

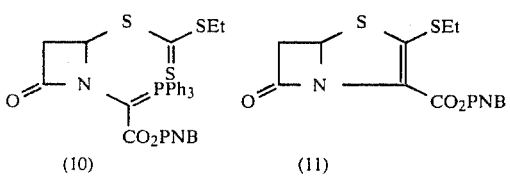

The phosphorane (10) (300 mg) was refluxed in xylene (300 ml) under argon for 6 hours using a heating mantle. The solution was concentrated in vacuo and the residue chromatographed on silica gel using 40–50% ethyl acetate/petroleum ether.

The desired penem (11) crystallised on evaporation to give cream coloured needles (84 mg, 51%) m.p. 131°. λmax (found M+ 366.0354 $C_{15}H_{14}N_2O_5S_2$ requires 366.0343) (EtOH) 340 nm (Em=11,500) 263 (16,800) νmax (CHCl₃) 1790, 1690 cm⁻¹ δppm (CDCl₃) 1.36 (3H, t, J=8) 2.96 (2H, qu J=8) 3.46 (1H, dd, J=16, 2 Hz) 3.83 (1H, dd, J=16, 4 Hz) 5.18 and 5.45 (2H, centres of AB qu J=14) 5.68 (1 H dd J=4, 2 Hz) 7.59 (2H, d, J=9 Hz) 8.17 (2H, d, J=9 Hz).

EXAMPLE 8

2-Ethylthiopenem-3-carboxylic acid

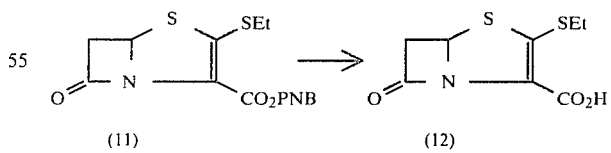

The p-nitrobenzyl ester (11) (80 mg) in dioxan (4 ml) was treated for two minutes with decolourising charcoal (50 mg) and was then filtered into a suspension of prehydrogenated 5% palladised charcoal catalyst (100 mg) in dioxan (8 ml) and water (2 ml).

After shaking 3 hours in an atmosphere of hydrogen the mixture was filtered and the filtrate treated with sodium hydrogen carbonate (18 mg leq.). The mixture was evaporated to low bulk and the residue was partitioned between ethyl acetate and water, using a little sodium chloride to break the emulsion. The aqueous layer was separated, acidified with citric acid and re-extracted with ethyl acetate. The ethyl acetate solution was washed with water, dried ($MgSO_4$) and evaporated in vacuo to give the desired free acid (12) (5 mg, 10%) λmax (EtOH) 256, 330 nm.

The minimum inhibitory concentrations of this compound to inhibit the growth of the following bacteria are:

| ORGANISM | μg/ml | |
|---|---|---|
| | AGAR[1] | BROTH[2] |
| Citrobacter freundii E8 | 5.0 | |
| Enterobacter cloacae NI | 5.0 | |
| Escherichia coli 0111 | 5.0 | 8.0 |
| Escherichia coli JT 39 | 12.5 | 16 |
| Klebsiella aerogenes A | 2.5 | 8.0 |
| Proteus mirabilis C977 | 12.5 | 16 |
| Proteus morganni I580 | 50 | |
| Proteus rettgeri WM16 | 50 | |
| Proteus vulgaris WO91 | >50 | |
| Pseudomonas aeruginosa A | >50 | >250 |
| Salmonella typhimurium CT10 | 5.0 | |
| Serratia marcescens US20 | 5.0 | |
| Shigella sonnei MB 11967 | 5.0 | |
| Bacillus subtilis A | 1.2 | |
| Staphylococcus aureus Oxford | 5.0 | |
| Staphylococcus aureus Russell | 5.0 | 1.6 |
| Staphylococcus aureus 1517 | 50 | |
| Streptococcus faecalis I | >50 | |
| Streptococcus pneumoniae CN33 | 0.2 | |
| Streptococcus pyogenes CN10 | — | |
| E. Coli ESS | 2.5 | |

1. DST agar + 10% horse blood — inoculum 0.001 ml of a $10^{-2}$ dilution for G + ve bacteria or a $10^{-4}$ dilution for G − ve organisms
2. Microtitre using Nutrient broth

EXAMPLE 9

4(2-ethoxycarbonylvinylthio)azetidin-2-one

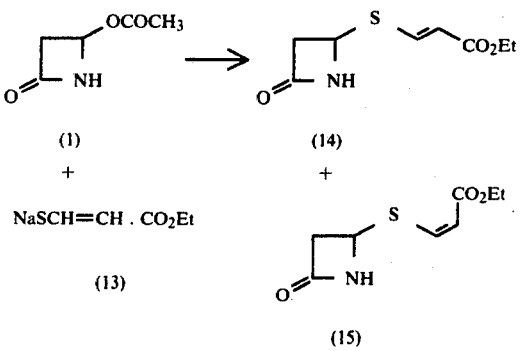

To a solution of acetoxyazetidin-2-one (4.2 g) in ethanol (60 ml) at 0° was added the sodium enethiolate (13; 5.0 g) in water (25 ml). After 3 hours, at 0° the mixture was evaporated to low bulk in vacuo and extracted with toluene. The toluene extract was chromatographed on silica gel eluting with 40-80% ethyl acetate/petroleum ether.

The first fraction to be eluted consisted of the trans-compound (14) obtained as a clear oil (2.08 g, 42%) (Found M+201.0481 $C_8H_{11}NO_3S$ requires 201.0459) νmax ($CHCl_3$) 3400, 3300 (b) 1780 (b) 1700, 1590 $cm^{-1}$ δppm ($CDCl_3$) 1.3 (3H, J=7) 2.95 (1H, dd, J=16, 2 Hz) 3.55 (1H, ddd J=16,16, 2 Hz) 4.17 (2H, qu. J=7H3) 5.10 (1H, dd, J=4, 2 Hz) 5.83 (1H, d J=16 Hz) 7.65 (1H, d J=16 Hz) 7.75 (1H, b. exch $D_2O$).

The second fraction to be eluted was the cis-compound (15) (0.82 g, 16%) white needles m.p. 91° ex ethyl acetate/petroleum.

(Found: C, 48.05; H, 5.38; N, 7.00. $C_8H_{11}NO_3S$ requires C, 47.76; H, 5.47; N, 6.96%). νmax ($CHCl_3$) 3400, 3300 (b) 1780, 1770, 1690, 1570 $cm^{-1}$ δppm ($CDCl_3$) 1.3 (3H, t J=$7H_3$) 3.0 (1H, dd, J=16, 2 Hz) 3.52 (1H, ddd, 16, 15, 2 Hz) 4.22 (2Hq, 7Hz) 4.99 (1H, dd, 5,2 Hz) 6.0 (1H, d, J=10 Hz) 7.25 (1H, d J=10 Hz) 7.4 (1H, bS exch $D_2O$).

EXAMPLE 10

1-(1-t-Butoxycarbonyl-1-hydroxy-methyl)-4(2-ethoxycarbonylvinylthio) azetidin-2-one

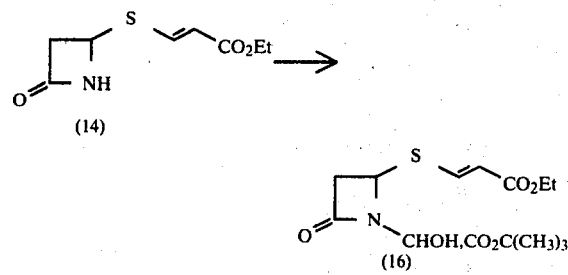

The trans ethoxycarbonylvinylthio-azetidinone (14), (0.77 g) and t-butyl glyoxylate (1.1 g, 1.6 eq) in benzene (20 ml) was refluxed overnight using a Dean & Stark water separator. The product (16) was isolated as in Example 2, it consisted of two diasterioisomers, total yield (1.21 g, 84%). The isomer first eluted from the chromatography column had νmax ($CHCl_7$) 3500, 1775, 1739, 1705, 1590 $cm^{-1}$ δppm ($CDCl_3$) 1.3 (3H, t, J=7 Hz) 1.5z (9H, 5) 3.02 (1H, dd, J=16, 2 Hz) 3.56 (1H dd, J=16, 4 Hz) 4.18 (qu, J=7 Hz) overlaying 4.3 (bd. exch $D_2O$) 5.0 (d J=6 Hz) together 2H, 5.0 (d J=6 Hz) overlaying 5.07 (dd J=2, 4 Hz) 2H together. 5.97 (1Hd J=16 Hz) 7.64 (1Hd, J=16 Hz).

The isomer last eluted had max ($CHCl_3$) 3500, 1775, 1730, 1705, 1590 $cm^{-1}$ δppm ($CDCl_3$) 1.3 (3H, t, J=7 Hz) 1.5 (9 HS) 3.04 (1H, dd, J=16, 2 Hz) 3.56 (1H, dd, J=16, 4 Hz) 4.2 (qu J=7 Hz) overlapping 4.4 (b.s. exch $D_2O$) together 2H, 5.2 (dd) J=4, 2 Hz) overlaying 5.42 (bd J=4 Hz) together 2H, 5.95 (iH, d, J=16 Hz) 7.6 (1H dd J=16 Hz).

EXAMPLE 11

1-(1-t-Butoxycarbonyl-1-triphenylphosphoranylidenemethyl)-4(2-ethoxycarbonylvinylthio) azetidin-2-one

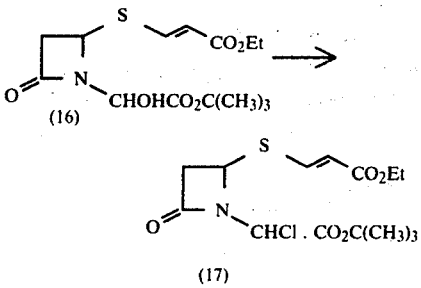

-continued

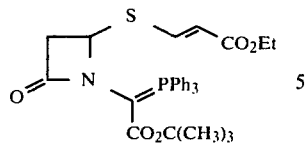
(18)

The t-butyl hydroxyester (16, mixed diastereoisomers) (1.088 g) was treated with thionyl chloride/lutidine by the method of Example 3. The chloride (17) was obtained as an oil (1.0 g) νmax (CHCl$_2$) 1785, 1740, 1705 cm$^{-1}$. This was treated with triphenyl phosphine/lutidine as in Example 3 to give the desired phosphorane (1.0 g, 50% from 16) as a gum νmax (CHCl$_3$) 1755, 170, 1630 cm$^{-1}$.

EXAMPLE 12 t-Butyl penem-3-carboxylate

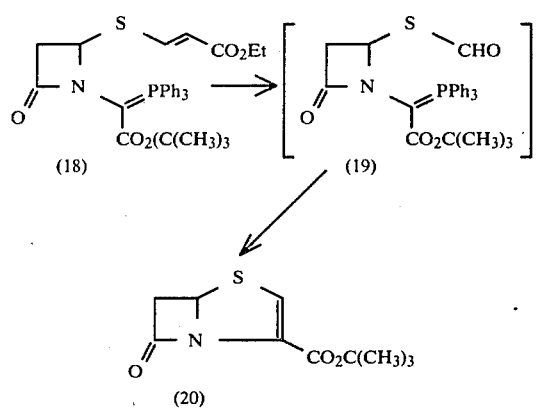

The phosphorane (18)(1.0 g) in ethyl acetate (40 ml) and trifluoroacetic acid (2.0 g 10 eq) was cooled in an acetone/CO$_2$ bath and ozonized oxygen was passed until a blue colour persisted (20 minutes) Excess of ozone was blown out with argon and triphenylphosphine (0.46 g 1 eq) was added. The mixture was allowed to reach 0° over ½ hour. Finally 10% aqueous sodium bicarbonate (60 ml) was added with vigorous stirring.

The solvent layer was separated, dried (MgSO$_4$), and evaporated; then the residue was chromatographed eluting with 40% ethyl acetate/petroleum ether. The desired penem ester (20) was obtained as white crystals m.p. 133°–135° (0.21 g, 58%) (Found: C, 52.8; H, 5.5; N, 6.0%, C$_{10}$H$_{13}$NO$_3$S requires C, 52.9; H, 5.7; N, 6.2%). νmax (CHCl$_3$) 1790, 1700, 1960 cm$^{-1}$ λmax (EtOH) 316 nm (Em=7.100) δppm (CDCl$_3$) 1.53 (9H, 5, But) 3.47 (1H dd J=16, 2 Hz) 3.90 (1H, dd J=16, 4 Hz) 5.79 (1H, dd J=4,2 Hz) 7.15 (1H, b.s.).

EXAMPLE 13

1-(1-pNitrobenzyloxycarbonyl-1-hydroxy-methyl)-4(2-ethoxy carbonylvinylthio) azetidin-2-one

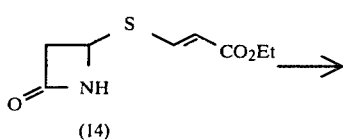
(14)

-continued

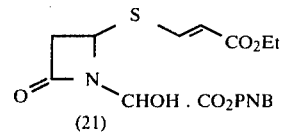
(21)

The trans ethoxycarbonylvinylazetidinone (14, 1.9 g) and p-nitrobenzyl glyoxylate (4.3 g 2 eq) were refluxed in benzene (50 ml) overnight using a Dean and Stark water separator. The product was isolated as in Example 2 (5.1 g). Effective separation from excess of glyoxylate was not achieved νmax (CHCl$_3$) 1775, 1750, 1605 cm$^{-1}$.

The mixture of diastereoisomers was used without purification for the succeeding stage.

EXAMPLE 14

1-(1-p-Nitrobenzylcarbonyl-1-triphenylphosphoranylidenemethyl)-4-(2-ethoxycarbonylvinylthio)azetidino-2-one

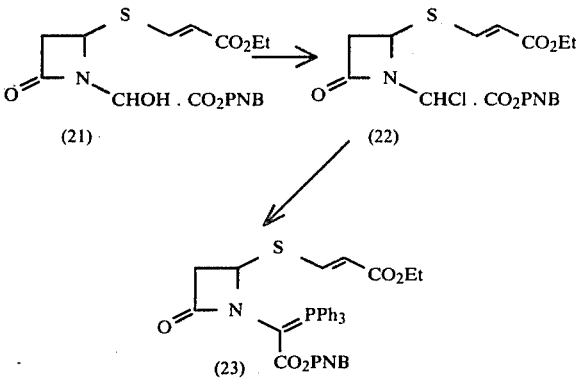

The nitrobenzyl hydroxy ester (21, 5.1 g) was treated first with SOCl$_2$/lutidine then with triphenylphosphine/lutidine as in the method of Example 3 to give the desired phosphorane (23) as an amorphous solid (4.89 g, 79% from compound 14 of Example 9) νmax (CHCl$_3$) 1755, 1700, 1625 cm$^{-1}$

EXAMPLE 15 p-Nitrobenzyl penem-3-carboxylate

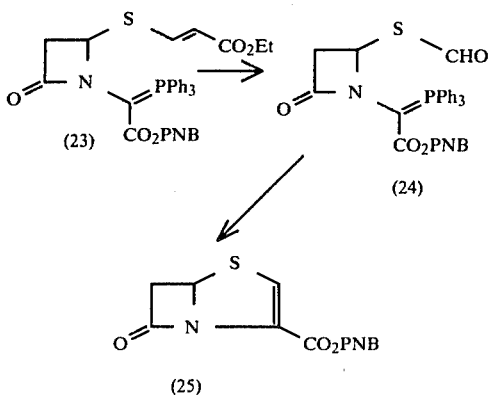

The phosphorane (23, 1.0 g) was treated with trifluoroacetic acid (4 ml) in ethyl acetate (20 ml) followed by ozonolysis as in Example 12. In this case, however, the ethyl acetate solution was kept at 50° for ½ hour to complete cyclisation to (25). The product was isolated by chromatography on silica gel eluting with methylene chloride to give the ester (25, 0.35 g 73%) [white needles m.p. 163°–165° (Found C, 51.0; H, 3.3; N, 9.1; S, 10.3% $C_{13}H_{10}N_2O_5S$ requires C, 50.98; H, 3.27; N, 9.15, S, 10.45%)] $\nu$max (EtOH) 319 nm Em=9250, $\nu$max (CHCl$_3$) 1800, 1715 cm$^{-1}$ δppm (CDCl$_3$) 3.57 (1H, ddd J=17,2,1) 3.95 (1H, ddd J=17 4.2) 5.22 and 5.45 (2H, AB qu J=14 Hz), 5.81 (1H, dd, J=4,2 Hz), 7.35 (1H, d, J=1Hz), 7.57 (2H, d J=9Hz) and 8.23 (2H, d, J=9Hz).

EXAMPLE 16

Penem-3-carboxylic acid and its sodium salt

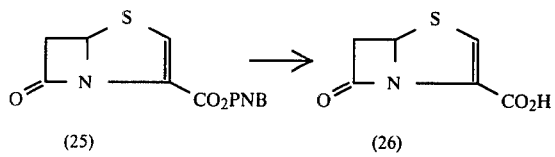

(25) (26)

The p-nitrobenzyl ester (25, 60 mg) was hydrogenated over prehydrogenated 5% Pd/C catalyst in dioxan (10 ml) and water (2 ml) at atmospheric pressure and room temperature for 1 hour. After filtration the solution was evaporated in vacuo to yield penam-3-carboxylic acid (26). This residue was redissolved in water (treated with sodium bicarbonate (16 mg. 1 eq)) and washed with ethyl acetate and again filtered. The aqueous filtrate was then evaporated in vacuum to give the sodium salt of penem-3-carboxylic acid (30 mg). $\lambda$max (EtOH) 302 nm (Em 5,300) $\nu$max (KBr) 3300–2700, 1765, 1600, 1560 cm$^{-1}$ δppm (D$_2$O) 3.55 (ddd j=16, 2, 1 Hz), 3.87 (ddd, J=16, 4, 1 Hz), 5.85 (dd J=4, 2 Hz) and 7.05 (t J=1 Hz).

EXAMPLE 17

1(1-Benzyloxycarbonyl-1-triphenylphosphoranylidenemethyl)-4-(2-ethoxycarbonylvinylthio)azetidin-2-one

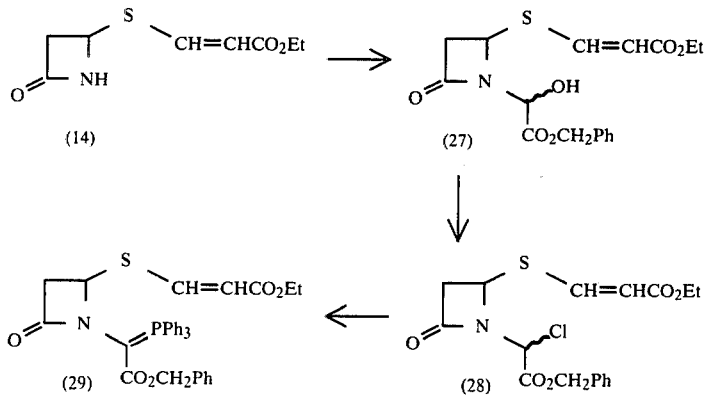

The azetidinone (14) (13.68 g) (a mixture of geometric isomers) and benzyl glyoxylate monohydrate (18.6 g) were refluxed in dry benzene (250 ml) for 3 hours with provision for the azeotropic removal of water (Dean and Stark). The mixture was evaporated and the residue was chromatographed on silica gel to give the hydroxy-ester (27), a mixture of isomers, contaminated with benzyl glyoxylate as an oil.

The crude hydroxy-ester (27) was dissolved in dry tetrahydrofuran (250 ml), cooled to −10° C., and treated with 2,6-lutidine (14.5 g) followed by the dropwise addition in 15 minutes of a solution of thionyl chloride (16.2 g) in dry tetrahydrofuran (10 ml). The mixture was stirred at −10° C. for a further 15 minutes, filtered, and evaporated. The residual oil was dissolved in dry toluene (100 ml), filtered, and evaporated to give the chloro-ester (28) as a crude viscous oil.

The crude chloride (28), triphenylphosphine (35.6 g) and 2,6-lutidine (8.7 g) were heated at 60° C. under argon in dry dioxan (250 ml) for 3 hours. The mixture was filtered, evaporated to low volume, and diluted with ethyl acetate (500 ml). The resulting solution was washed with N. hydrochloric acid (50 ml) and brine (3×50 ml). The dried (MgSO$_4$) organic layer was evaporated and the residue chromatographed on silica gel eluting with ethyl acetate/petroleum ether 60°–80° C. mixtures to give the phosphorane (29) (19.1 g) as an amorphous solid, $\nu$max 1755, 1695, 1620, 1585 cm$^{-1}$.

EXAMPLE 18

Benzyl penem-3-carboxylate

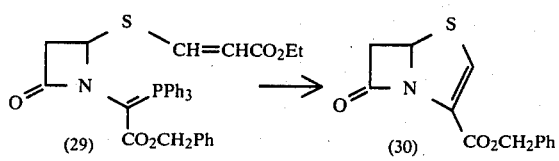

The phosphorane (29) (1.218 g) was dissolved in ethyl acetate (20 ml) and treated with trifluoroacetic acid (1.52 ml). The mixture was kept at room temperature for 5 minutes, cooled to −76° C., and ozone passed till pale blue colour persisted. The excess ozone was removed by passage of argon and the mixture was treated with a solution of triphenylphosphine (524 mg) in ethyl acetate (5 ml). The mixture was allowed to attain 0° C. and was made slightly alkaline with saturated sodium bicarbonate solution. The organic layer was separated and washed with brine (3×5 ml) The dried (MgSO$_4$) organic layer was heated at 50° C. under argon for 30 minutes. The mixture was evaporated and the residue chromatographed on silica gel, eluting with ethyl acetate/petroleum ether 60°–80° C. mixtures, to give the penem benzyl ester (30) (333 mg) as a solid, m.p. 118°–119° C. (prisms from ethyl acetate/petroleum ether 60°–80° C.). $\lambda$max (EtOH) 260 (Em 2950) and 319 nm (7540); $\nu$max (CHCl$_3$) 1795 and 1715 cm$^{-1}$; δppm (CDCl$_3$) 3.49(1H, ddd, J 16, 2, and 2 Hz), 3.83(1H, dd, J 16 and 4 Hz), 5.23(2H, s), 5.74(1H, dd, J 4 and 2 Hz), 7.24(1H, d, J 2 Hz), 7.35(5H, s). (Found: C, 59.6; H, 4.1; N, 5.2; S, 12.3%; M+, 261.0433. C$_{13}$H$_{11}$NO$_3$S requires C, 59.7; H, 4.2; N, 5.4; S, 12.3%; M, 261.0459).

EXAMPLE 19

Benzyl 2-methylthiopenem-3-carboxylate

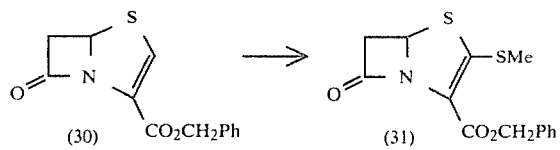

Method (a)

The penem ester (30) (200 mg) was dissolved in dry tetrahydrofuran (8 ml), cooled to −95° C. (toluene/liquid nitrogen), and treated with n-butyl lithium (0.48 ml of a 1.6 M solution of n-hexane). The mixture was immediately treated with a solution of methyl methanethiosulphonate (108 mg) in dry tetrahydrofuran (0.5 ml). After stirring at −95° C. for a further ½ minute the mixture was made slightly acid with a solution of acetic acid in tetrahydrofuran. The mixture was diluted with ethyl acetate (30 ml) and washed with dilute sodium bicarbonate solution and brine. The dried (MgSO$_4$) organic layer was evaporated and the residue chromatographed on silica gel eluting with ethyl acetate/petroleum ether 60°-80° C. mixtures to give the 2-methylthiopenem ester (31) (144 mg) as a solid, m.p. 136°-137° C. (needles from ethyl acetate/petroleum ether 60°-80° C.). λmax (EtOH) 257 (Em, 6370) and 339 n.m. (8870); νmax (CHCl$_3$) 1795 and 1685 cm$^{-1}$; δppm (CDCl$_3$) 2.50(3H, s), 3.43(1H, dd, J 16 and 2 Hz), 3.79(1H, dd, J4 and 2 Hz), 7.20-7.50 (5H, s). (Found: C, 54.6; H, 4.4; N, 4.6; S, 20.8%; M+, 307.0310. C$_{14}$H$_{13}$NO$_3$S$_2$ requires C, 54.7; H, 4.2; N, 4.6; S, 20.9%; M, 307.0337).

Method (b)

The penem ester (30) (50 mg) was dissolved in dry tetrahydrofuran (2 ml), cooled to −95° C., and treated with n-butyl lithium (0.12 ml of a 1.6 M solution in n-hexane). The mixture was immediately treated with a solution of methanesulphenyl chloride (17 mg) (prepared from dimethyl disulphide by treatment with sulphuryl chloride followed by distillation of the product) in dry tetrahydrofuran (0.5 ml). After stirring at −95° C. for a further ½ minute the mixture was worked up as before to give the 2-methylthipenem ester (31) (14 mg) as a solid.

EXAMPLE 20 t-Butyldiphenylsilyl penem-3-carboxylate

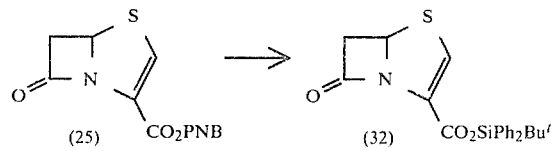

The penem p-nitrobenzyl ester (25) (1.0 g) was dissolved in a mixture of dioxan (80 ml) and water (20 ml) and was hydrogenated over 10% palladium on charcoal (1.50 g) at N.T.P. After 40 minutes further 10% palladium on charcoal (1.0 g) was added and the hydrogenation was continued for 40 minutes. The mixture was filtered through Kieselguhr, the residue being washed with a little dioxan. The combined filtrates were evaporated to low volume and the residue was re-evaporated from ethanol (2×10 ml) and dry toluene (2×20 ml) and finally dried under vacuum. The crude product thus obtained was stirred in dry methylene chloride (50 ml) containing triethylamine (660 mg) and was treated dropwise in 10 minutes with a solution of t-butyldiphenylsilyl chloride (1.79 g) in dry methylene chloride (10 ml). The mixture was stirred at room temperature for 30 minutes, filtered, and evaporated. The residue was re-dissolved in ethyl acetate, filtered, and washed with brine. The dried (MgSO$_4$) organic layer was evaporated and the residue chromatographed on silica gel eluting with ethyl acetate/petroleum ether 60°-80° C. mixtures to give the penem silyl ester (32) (385 mg) as a solid, m.p. 138°-139° C. (cubes from ethyl acetate/petroleum ether 60°-80° C.). λmax (EtOH) 261(Em 3460), 266(3400), 272(2730), and 322 n.m. (8390); νmax (CHCl$_3$) 1800 and 1695 cm$^{-1}$; δppm (CDCl$_3$) 1.13(9H, s), 3.53(1H, ddd, J 16, 2 and approximately 1 Hz), 3.87(1H, dd, J 16 and 4 Hz), 5.80(1H, dd, J 4 and 2 Hz), 7.25-7.80(11H, m). (Found: C, 64.5; H, 5.5; N, 3.4; S, 7.6%. C$_{22}$H$_{23}$NO$_3$SSi requires C, 64.6; H, 5.6; N, 3.4; S, 7.8%).

EXAMPLE 21 t-Butyldiphenylsilyl 2-methylthiopenem-3-carboxylate

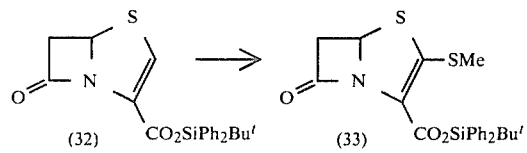

The penem silyl ester (32) (200 mg) was dissolved in dry tetrahydrofuran (5 ml) cooled to −95° C. (toluene/liquid nitrogen), and treated with n-butyl lithium (0.31 ml of a 1.6 M solution in n-hexane). The mixture was stirred at −95° C. for 2 minutes and treated with a solution of methyl methanethiosulphonate (68 mg) in dry tetrahydrofuran (0.5 ml). It was stirred at −95° C. for a further ½ minute and made slightly acidic with a solution of acetic acid in tetrahydrofuran. The mixture was diluted with ethyl acetate (20 ml) and was washed with dilute sodium bicarbonate solution and brine. The dried (MgSO$_4$) organic layer was evaporated and the residue chromatographed on silica gel eluting with ethyl acetate/petroleum ether 60°-80° C. mixtures to give in addition to recovered starting material (68 mg) the desired 2-methylthiopenam ester (33) contaminated with methyl methanethiosulphonate. Trituration of the crude product with petroleum ether 60°-80° C. (2×1 ml) and petroleum ether 60°-80° C./ether (1:1, 1 ml) gave a solid which was re-chromatographed on silica gel to give pure 2-methylthiopenem ester (33) (53 mg) as a solid, m.p. 143°-145° C. (rods ex ethyl acetate/petroleum ether 60°-80° C.). λmax (EtOH) 260(Em, 8150) and 344 n.m. (10,600); νmax (CHCl$_3$) 1795 and 1670 cm$^{-1}$; δppm (CDCl$_3$) 1.12(9H, s), 2.45 (3H, s), 3.43(1H, dd, J 16 and 2 Hz), 3.81(1H, dd, J16 and 4 Hz), 5.68(1H, dd, J 4 and 2 Hz), 7.25-7.80(10H, m). (Found: M+, 455.1029. C$_{23}$H$_{25}$NO$_3$S$_2$Si requires M, 455.1043).

EXAMPLE 22

Potassium penem-3-carboxylate

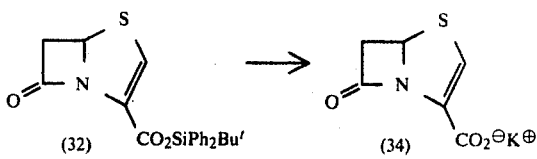

The penem silyl ester (32) (62 mg) was stirred in dry tetrahydrofuran (1.5 ml) containing anhydrous potassium fluoride (9 mg) and 18-Crown-6 (4 mg) at room temperature for 90 minutes. The mixture was evaporated and the residue was triturated with dry ether to give the potassium salt (34) (30 mg) as a buff coloured solid. λmax (EtOH) 264 and 301 n.m. νmax (KBr) 3400 broad, 1770, 1595, 1560 cm$^{-1}$; δppm (D$_2$O) 3.46(1H, dd, J 16 and 2 Hz), 3.81(1H, dd, J 16 and 4 Hz), 5.78(1H, dd, J 4 and 2 Hz), 7.09(1H, s), a signal at 3.62 ppm indicated the presence of 18-Crown-6 as contaminent.

The minimum inhibitory concentrations of this compound to inhibit the growth of the following bacteria are:

| ORGANISM | μg/ml | |
|---|---|---|
|  | AGAR[1] | BROTH[2] |
| *Citrobacter freundii* E8 | 25 |  |
| *Enterobacter cloacae* N1 | 25 |  |
| *Escherichia coli* O111 | 25 | 4.0 |
| *Escherichia coli* JT 39 | 25 | 8.0 |
| *Klebsiella aerogenes* A | 25 | 8.0 |
| *Proteus mirabilis* C977 | 25 | 16 |
| *Proteus morganii* I580 | 25 |  |
| *Proteus rettgeri* WM16 | 50 |  |
| *Proteus vulgaris* WO91 | 25 |  |
| *Pseudomonas aeruginosa* A | 50 | 8.0 |
| *Salmonella typhimurium* CT10 | 25 | 16 |
| *Serratia marcescens* US20 | 25 |  |
| *Shigella sonnei* MB 11967 | 25 |  |
| *Vacillus subtilis* A | 25 |  |
| *Staphylococcus aureus* Oxford | 25 | 8.0 |
| *Staphylococcus aureus* Russell | 25 | 16 |
| *Staphylococcus aureus* 1517 | >100 |  |
| *Streptococcus faecalis* I | >100 |  |
| *Streptococcus pneumoniae* CN33 | 10 |  |
| *Streptococcus pyogenes* CN10 | 25 |  |
| *Escherichia coli* ESS | 25 |  |

| 1. DST agar + 10% horse blood | inoculum 0.001 ml of a 10$^{-2}$ dilution for G + ve bacteria or a 10$^{-4}$ dilution for G − ve organisms |
|---|---|
| 2. Microtitre using Nutrient broth | |

EXAMPLE 23

Potassium 2-methylthiopenem-3-carboxylate

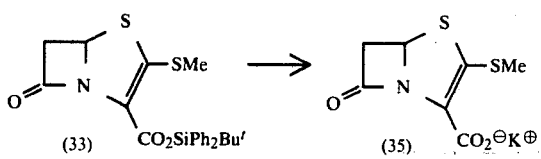

The 2-methylthiopenem silyl ester (33) (53 mg) was stirred in dry tetrahydrofuran (1.5 ml) containing anhydrous potassium fluoride (7 mg) and 18-crown-6 (3 mg) at room temperature for 90 minutes. Anhydrous potassium fluoride (2 mg) was added and the reaction mixture was stirred for a further 30 minutes. The mixture was evaporated and the residue triturated with dry ether to give the potassium salt (35) (33 mg) as a buff coloured solid. λmax (EtOH) 244, 275(inflection), and 320 n.m. νmax (KBr) 3440 broad, 1760, 1580, 1520 cm$^{-1}$; δppm (D$_2$O) 2.44(3H, s), 3.41(1H, dd, J 16 and 2 Hz), 3.78(1H, dd, J16 and 4 Hz), 5.67(1H, dd, J4 and 2 Hz), a signal at 3.62 ppm indicated the presence of 18-crown-6 as contaminent.

The minimum inhibitory concentrations of this compound to inhibit the growth of the following bacteria are:

| ORGANISM | μg/ml | |
|---|---|---|
|  | AGAR[1] | BROTH[2] |
| *Citrobacter freundii* E8 | 2.5 |  |
| *Enterobacter cloacae* N1 | 5.0 |  |
| *Escherichia coli* O111 | 5.0 | 4.0 |
| *Escherichia coli* JT 39 | 5.0 | 4.0 |
| *Klebsiella aerogenes* A | 5.0 | 4.0 |
| *Proteus mirabilis* C977 | 10 | 8.0 |
| *Proteus morganii* I580 | 25 |  |
| *Proteus rettgeri* WM16 | 25 |  |
| *Proteus vulgaris* WO91 | 50 |  |
| *pseudomonas aeruginosa* A | 100 | 250 |
| *Salmonella typhimurium* CT10 | 5.0 | 8.0 |
| *Serratia marcescens* US20 | 5.0 |  |
| *Shigella sonnei* MB 11967 | 5.0 |  |
| *Bacillus subtilis* A | 2.5 |  |
| *Staphylococcus aureus* Oxford | 1.0 | <0.2 |
| *Staphylococcus aureus* Russell | 2.5 | <0.2 |
| *Staphylococcus aureus* 1517 | 25 |  |
| *Streptococcus faecalis* I | 100 |  |
| *Streptococcus pneumoniae* CN33 | — |  |
| *Streptococcus pyogenes* CN10 | 1.0 |  |
| *Escherichia coli* ESS | 2.5 |  |

| 1. DST agar + 10% horse blood | inoculum 0.001 ml of a 10$^{-2}$ dilution for G + ve bacteria or a 10$^{-4}$ dilution for G-ve organisms. |
|---|---|
| 2. Microtitre using Nutrient broth | |

EXAMPLE 24 t-Butyldiphenylsilyl 2-phenylthiopenem-3-carboxylate

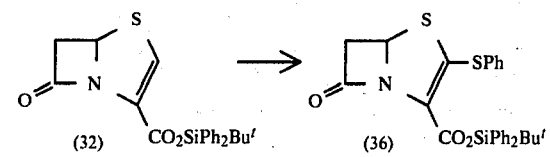

The penem silyl ester (32) (100 mg) was dissolved in dry tetrahydrofuran (2 ml), cooled to −95° C. (toluene/liquid nitrogen), and treated with n-butyl lithium (0.153 ml) of a 1.6 M solution in n-hexane). The mixture was stirred at −95° C. for 2 minutes and treated with a solution of benzenesulphenyl chloride (39 mg) in dry tetrahydrofuran (0.2 ml). After stirring at −95° C. for a further 2 minutes the mixture was diluted with ethyl acetate (10 ml) and washed with brine. The dried (MgSO$_4$) organic layer was evaporated and the residue chromatographed on silica gel eluting with diethyl ether/petroleum ether 60°-80° C. mixtures to give in addition to recovered starting material (7 mg) the desired 2-phenylthiopenem ester (36) (8 mg) as an amorphous solid, λ max (EtOH) 258 (Em 6,400) and 334 nm (7,600); ν max (CHCl$_3$) 1795 and 1675 cm$^{-1}$; δppm (CDCl$_3$) 1.15 (9H, s), 3.32 (1H, dd, J 16 and 2 Hz), 3.71 (1H, dd, J 16 and 4 Hz), 5.50 (1H, dd, J 4 and 2 Hz), 7.15–7.80 (15H, m). [Found: M+-57 (M-C4H9), 460.0516. C24H18NO3S2Si requires M, 460.0497].

EXAMPLE 25

Potassium 2-phenylthiopenem-3-carboxylate

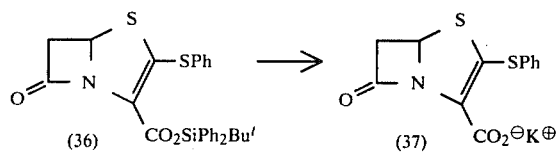

The 2-phenylthiopenem silyl ester (36) (8 mg) was stirred in dry tetrahydrofuran (0.5 ml) containing anhydrous potassium fluoride (0.9 mg) and 18-crown-6 (0.4 mg) at room temperature for 2 hours. The mixture was evaporated and the residue triturated with dry ether to give the desired potassium salt (37) (3.4 mg) as a solid, λ max (EtOH) 312 nm.

The minimum inhibitory concentrations of this compound to inhibit the growth of the following bacteria are:

| ORGANISM | AGAR[1] | BROTH[2] |
|---|---|---|
| *Citrobacter freundii* E8 | 25 | |
| *Enterobacter cloacae* N1 | 50 | |
| *Escherichia coli* O111 | 25 | 31 |
| *Escherichia coli* JT 39 | 50 | 62 |
| *Klebsiella aerogenes* A | 12.5 | 4.0 |
| *Proteus mirabilis* C977 | 25 | 8.0 |
| *Proteus morganii* I580 | 25 | |
| *Proteus rettgeri* WM16 | — | |
| *Proteus vulgaris* WO91 | 25 | |
| *Pseudomonas aeruginosa* A | >100 | 125 |
| *Salmonella typhimurium* CT10 | 50 | |
| *Serratia marcescens* US20 | 50 | |
| *Shigella sonnei* MB 11967 | 100 | |
| *Bacillus subtilis* A | 3.1 | |
| *Staphylococcus aureus* Oxford | 6.2 | 2.0 |
| *Staphylococcus aureus* Russell | 12.5 | 4.0 |
| *Staphylococcus aureus* 1517 | — | |
| *Streptococcus faecalis* I | — | |
| *Streptococcus pneumoniae* CN33 | 0.8 | |
| *Streptococcus pyogenes* CN10 | 0.8 | |
| *Escherichia coli* ESS | 6.2 | |

1. DST agar + 10% horse blood
2. Microtitre using Nutrient broth inoculum 0.001 ml of a $10^{-2}$ dilution for G + ve bacteria or a $10^{-4}$ dilution for G − ve organisms

EXAMPLE 26

Sodium 2-(2-acetamidoethylthio)penem-3-carboxylate and Sodium 2(2-aminoethylthio)penem-3-carboxylate

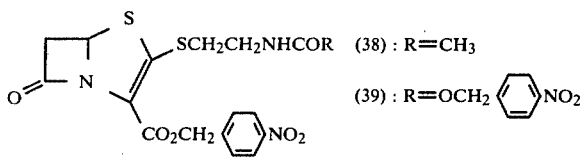

Using the general methods described herein the following penem esters were prepared:

Compound (38); m.p. 153°–154°; $\lambda_{max}$ (EtOH) 336 nm (E 10,600) and 260 nm (E 15,700); $\nu_{max}$ 3450, 1800, 1690 sh, 1675, 1610 cm$^{-1}$. δ ppm 2.0 (3H, s, CH3CO), 3.03–3.70 (5H, m, CH2CH2 and C6-H trans), 3.87 (1H, dd, J 16 and 4 Hz, C6-H cis), 5.2 and 5.47 (2H, ABq, J 14 Hz, CH2Ar), 5.73 (1H, dd, J 4 and 2 Hz, C5-H), 5.95 (1H, bs, NH), 7.60 (2H, d, J 9 Hz, aromatic) and 8.2 (2H, d, J 9 Hz, aromatic). (Found C; 48.3, H, 4.0; N, 9.6. C17H17N3O6S2 requires C, 48.3; H, 3.8; N, 9.9%).

Compound (39); m.p. 174°–178°; $\lambda_{max}$ (EtOH) 335 nm (E 3,400) and 263 nm (E 8,600); $\nu_{max}$ 3450, 1795, 1720b and 1610 cm$^{-1}$. δ p.p.m 1.5 (1H, s, exch. D2O, NH), 3.0–3.65 (5H, m, CH2CH2 and C5-H trans), 3.85 (1H, dd, J 16 and 4 Hz, C5-H cis), 5.20 and 5.45 (4H, CH2Ar), 5.67 (1H, dd, J 4 and 2 Hz, C5-H), 7.47 and 7.60 (4H, 2d, J 8 Hz, aromatic) and 8.23 (4H, d, J 8 Hz aromatic).

Hydrogenolysis of compound (38) by the general procedure of Example 8 followed by Biogel chromatography gave the sodium salt (40) in 67% yield; $\lambda_{max}$ (EtOH) 318 nm (E 5,100); δ ppm (D2O) 1.95 (s, COCH3), 2.7–3.5 (m, CH2CH2), 3.45 (dd, J 16 and 2 Hz, C6-H trans), 3.72 (dd, J 16 and 4 Hz, C6-H cis), 5.68 (dd, J 4 and 2 Hz, C5-H).

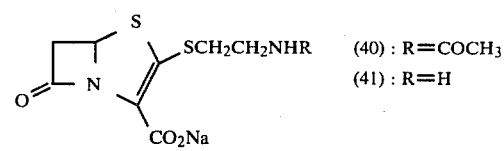

(40) : R=COCH3
(41) : R=H

Hydrogenolysis of compound (39) similarly gave sodium 2-(2-aminoethylthio)penem-3-carboxylate (41), $\lambda_{max}$ (EtOH) 319 nm (E 5,470).

Antibacterial tests on penems (40) and (41) indicated the minimum inhibitory concentrations required to inhibit growth of the following bacteria to be:

| | Compound (40) | | Compound (41) | |
|---|---|---|---|---|
| | Agar[1] | Broth[2] | Agar[1] | Broth[2] |
| Organism | μg/ml | | μg/ml | |
| *Citrobacter freundii* E8 | 2.5 | | 12.5 | |
| *Enterobacter cloacae* N1 | 25 | | 100 | |
| *Escherichia coli* O111 | 5 | 1.6 | 12.5 | 8 |
| *Escherichia coli* JT 39 | 5 | 3.1 | 25 | 8 |
| *Klebsiella aerogenes* A | 2.5 | 1.6 | 12.5 | 16 |
| *Proteus mirabilis* C977 | 25 | | 25 | 31 |
| *Proteus morganii* I580 | 25 | | 25 | |
| *Proteus rettgeri* WM16 | 25 | | 50 | |
| *Proteus vulgaris* W091 | 10 | | 100 | |
| *Pseudomonas aeruginosa* A | >100 | 100 | >100 | 125 |
| *Salmonella typhimurium* CT10 | 2.5 | | 12.5 | |
| *Serratia marcescens* US20 | 5 | | 25 | |
| *Shigella sonnei* MB 11967 | 2.5 | | 12.5 | |
| *Bacillus subtilis* A | — | | 25 | |
| *Staph. aureus* Oxford | 2.5 | 0.4 | 3.1 | 0.5 |
| *Staph. aureus* Russell | 10 | 3.1 | 12.5 | 8 |
| *Staph. aureus* 1517 | 100 | | >100 | |
| *Staph. faecalis* I | 100 | | >100 | |
| *Strep. pneumoniae* CN33 | — | | 0.8 | |
| *Strep. pyogenes* CN10 | 0.5 | | — | |
| *E. coli* ESS | 5 | | 12.5 | |

1. DST ager + 10% horse blood
2. Microtitre using Nutrient broth inoculum 0.001 ml of a $10^{-2}$ dilution for G + ve bacteria or a $10^{-4}$ dilution for G − ve organisms.

What we claim is:

1. A process for the preparation of the compounds of the formula (II):

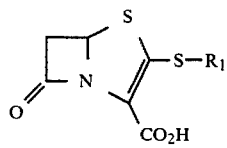

and salts and esters thereof convertible by hydrogenolysis, hydrolysis or fluoride ion wherein $R_1$ is a hydrocarbon group of up to 12 carbon atoms and which optionally also has up to 4 heteroatoms selected from oxygen, nitrogen, sulphur or chlorine and bromine which process is carried out by the reaction of an ester of a compound of the formula (III):

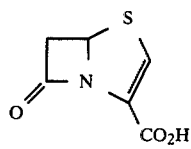

with one equivalent of a strong base of low nucleophilicity and thereafter with a compound of the formula (IV) or (V):

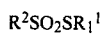

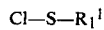

wherein $R_1^1$ is a group $R_1$ in which any amino substituent is protected and $R^2$ is an alkyl group of 1–4 carbon atoms optionally substituted by a phenyl group or is a phenyl group optionally substituted by an alkyl group of 1–4 carbon atoms and thereafter when desired converting the ester moiety to the acid form of the formula (II) or a salt thereof and removing the protecting group from any protected amino group present in $R_1^1$.

2. A process as claimed in claim 1 adapted to the preparation of a compound of the formula (II) wherein $R_1$ is an alkyl group of up to 4 carbon atoms; an alkenyl group of up to 4 carbon atoms; an alkyl group of up to 4 carbon atoms substituted other than on the α-carbon atom by an amino or acetylamino group; an alkyl group of up to 4 carbon atoms substituted by an alkoxycarbonyl group wherein the alkoxy part has up to 4 carbon atoms; an alkenyl group of up to 4 carbon atoms substituted other than on the α-carbon atom by an acetylamino group; an alkenyl group of up to 4 carbon atoms substituted by an alkoxycarbonyl group wherein the alkoxy part contains up to 4 carbon atoms; a phenyl group; a phenyl group substituted by a methyl, amino, alkoxycarbonyl wherein the alkoxy part has up to 4 carbon atoms; acetamino or methoxyl groups or by a chlorine or bromine atom; a pyridyl group; or a pyrimidyl group.

3. A process as claimed in claim 1 adapted to the preparation of a compound of the formula (II) wherein $R_1$ is a methyl, ethyl, n-propyl, β-aminoethyl, β-acetamidoethyl or phenyl group.

4. A process as claimed in claim 1 wherein the convertible ester of the compound of the formula (III) is the diphenyltertiarybutylsilyl ester.

5. A process as claimed in claim 1 wherein the base used is n-butyl lithium.

6. A process as claimed in claim 5 carried out at a depressed temperature in dry tetrahydrofuran.

7. A process as claimed in claim 4 wherein the ester is converted by treatment with anhydrous potassium fluoride to yield the potassium salt of a compound of the formula (II).

8. The process of claim 1 wherein the ester of formula (III) is the diphenyltertiarybutyl silyl ester.

* * * * *